US00PP32712P2

(12) United States Plant Patent
Hansen

(10) Patent No.: US PP32,712 P2
(45) Date of Patent: Dec. 29, 2020

(54) **X *MANGAVE* PLANT NAMED 'WIGGING OUT'**

(50) Latin Name: ***X Mangave* hybrid**
Varietal Denomination: Wigging Out

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,336

(22) Filed: Mar. 23, 2020

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 5/12; A01H 5/02; A01H 5/00
See application file for complete search history.

*Primary Examiner* — Kent L Bell

(57) ABSTRACT

A new and unique X *Mangave* plant named 'Wigging Out' characterized by numerous, long, narrow, horizontal leaves with variegated creamy-white margins and dark green centers and irregular dark-burgundy spotting in the center and purplish-red in the margins covering large portions of leaves especially when grown in high ultraviolet light exposure. Leaves have minimal marginal spines and apical spines are flexible. Growth rate is moderate. 'Wigging Out' is suitable for the garden or as a potted plant in the garden or home.

1 Drawing Sheet

Botanical classification: X *Mangave* hybrid.
Variety denomination: 'Wigging Out'.

STATEMENT REGARDING PRIOR DISCLOSURES UNDER 37 CFR 1.77(B)(6)

No plants of x *Mangave* 'Wigging Out' have been sold, in this country or anywhere in the world, nor has any disclosure of the new plant been made as of the filing of this application.

BACKGROUND OF THE INVENTION

The present invention relates to the new and distinct X *Mangave* hybrid plant, X *Mangave* 'Wigging Out' was discovered by the inventor at a wholesale perennial nursery in Zeeland, Mich., USA as a whole plant mutation of x *Mangave* 'Bad Hair Day' U.S. Plant Pat. No. 30,279, discovered on Apr. 1, 2019. Through trials at the same nursery the new plant was assigned the code 19-SP-MANG-818. The new plant has been successfully asexually propagated initially by sterile shoot-tip tissue culture at the same nursery in Zeeland, Mich. For those skilled in the art this method of asexual propagation system has been found to produce stable and identical plants that maintain all the unique characteristics of the original plant in successive generations.

BRIEF SUMMARY OF THE INVENTION

X *Mangave* 'Wigging Out' differs from its parent as well as all other *Manfreda, Agave* and X *Mangave* known to the applicant. The mutation parent, 'Bad Hair Day' lacks the creamy-white variegated margin. The most similar known cultivar is *Agave geminiflora* 'Leaping Lizard' (not patented). 'Leaping Lizard' has slightly narrower and thicker leaves with much slower growth rate. 'Snow Leopard' U.S.

Plant Pat. No. 31,137 and 'Navajo Princess' U.S. Plant Pat. No. 31,136 are x *Mangave* cultivars with creamy-white variegated margins. Both have larger habit with less arching, and leaves that are broader and have larger marginal teeth.

'Wigging Out' is unique from all of the above cultivars and all *Agave*, X *Mangave*, and *Manfreda* known to the inventor by the following combined traits:

1. Numerous, long, narrow, gracefully arching foliage;
2. Foliage develops irregular, dark-burgundy spotting in leaf center and purplish-red in the margins especially in high ultraviolet light exposure;
3. Leaf margins are variegated with creamy-white and have deep green centers.
4. The new plant has minimal marginal spines and terminal spines are flexible through drying;
5. Moderate growth rate.

BRIEF DESCRIPTION OF THE DRAWINGS

The photographs of x Mangave 'Wigging Out' demonstrate the overall appearance of the new plant including the unique traits as a one-year-old plant grown in a container in a greenhouse in low ultraviolet light in Zeeland, Mich. with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
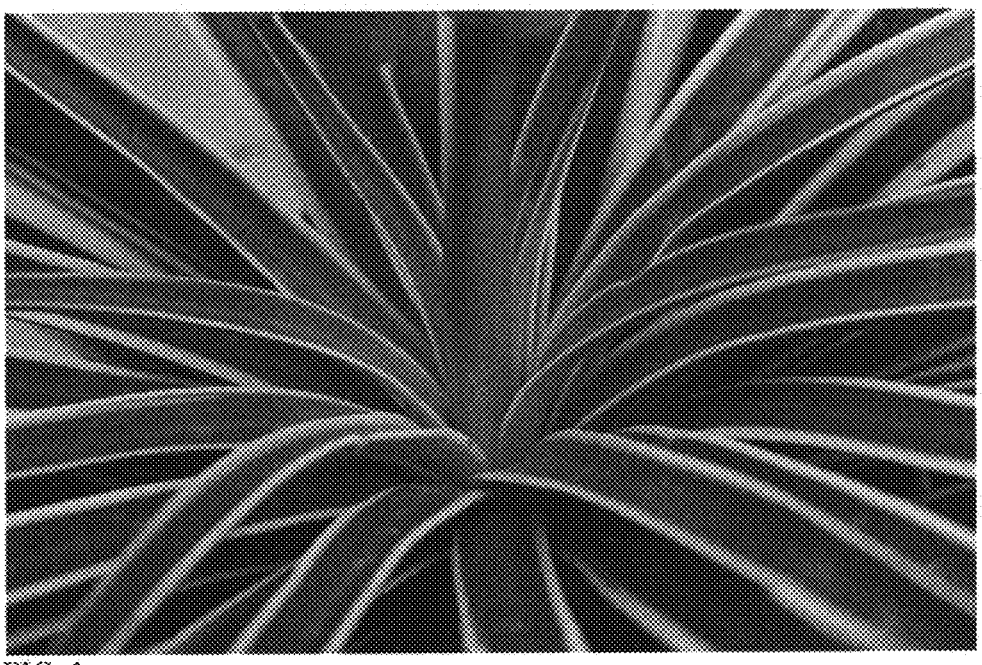
FIG. 1 shows a close-up of the foliage of the new plant.
Figure 2:
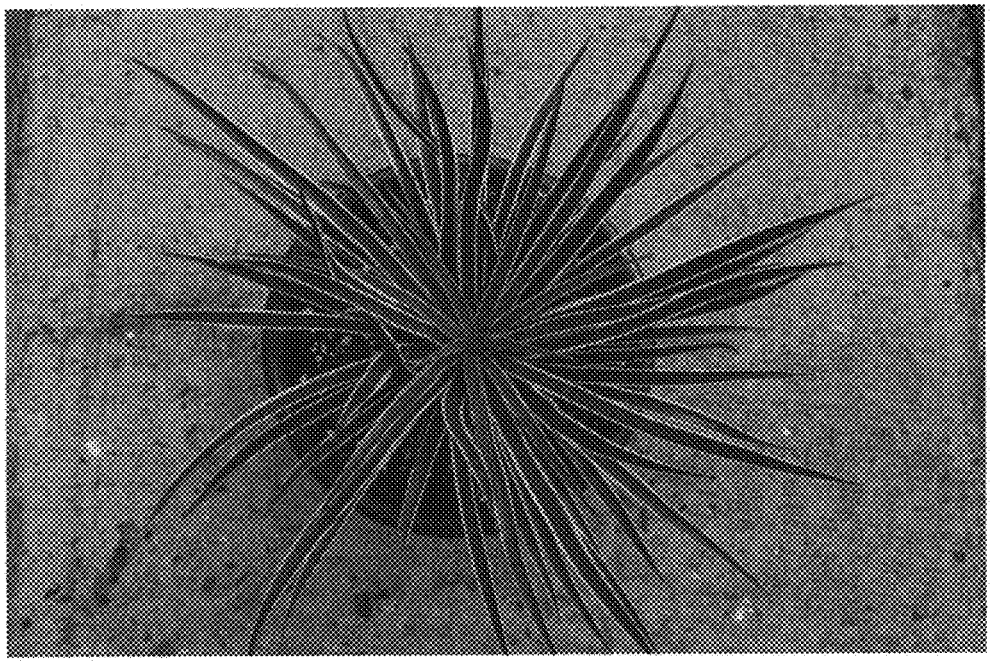
FIG. 2 shows the habit of the new plant from above grown in a container.

The following descriptions and color references are based on the 2015 edition of The Royal Horticultural Society Colour Chart except where common dictionary terms are used. The new plant, X *Mangave* 'Wigging Out', has not been observed under all possible environments. The phenotype may vary slightly with different environmental conditions, such as temperature, light, fertility, moisture and maturity levels, but without any change in the genotype. The following observations and size descriptions are of a one-year old plant in a commercial wholesale greenhouse in Zeeland, Mich. and also with a season of outdoor growth receiving supplemental water and fertilizer as needed.

Parentage: A whole plant mutation of 'Bad Hair Day';

Propagation: Division of side shoots and sterile shoot-tip tissue culture;

Time to initiate roots from tissue culture: About three weeks;

Growth rate: Moderate;

Crop time: About 16 to 20 weeks to finish in a 3.8 liter container from a 35 mm tissue culture growing at about 21° C.;

Rooting habit: Fleshy, lightly branching, with roots up to 20 cm long; Root color: nearest RHS 158C;

Plant shape and habit: Succulent herbaceous perennial with basal rosettes of about 66 leaves per plant, radially emerging from central rhizome extending below the base of the plant and drooping in maturity when grown in containers, producing a radially-symmetrical, rounded mound;

Plant size: Foliage height about 28.0 cm tall from soil line to the top of emerging leaves and about 32.0 cm wide at the widest point slightly below soil line in container and drooping to about 5.0 cm below soil line when grown in elevated containers;

Foliage description: Gladiate to linear; simple; margins finely dentate; apex narrowly acute; base truncate, sessile, clasping; flattened; bi-laterally symmetrical; with dense, irregular, burgundy spotting from 0.5 mm to about 3.0 mm across, more pronounced on adaxial surface in high ultraviolet light; glaucous both surfaces;

Leaf size: To about 25.0 cm long, about 12.0 cm wide at base and about 2.0 mm thick; average about 23.0 cm long, about 10.0 cm wide and about 2.0 mm thick;

Foliage fragrance: None observed;

Leaf blade color:

*Adaxial* (*mature*).—In low ultraviolet light margin nearest RHS 155C and in high ultraviolet light developing variable overtones of nearest RHS 186A and RHS 183D; center nearest RHS 137A and in high ultraviolet light exposure nearest RHS 146D with blush of nearest RHS N186C and spots of a blend between RHS N186C and RHS N187A becoming more dense and numerous with greater ultraviolet light exposure.

*Abaxial* (*mature*).—In low ultraviolet light exposure margin nearest RHS 155C and in high ultraviolet light developing overtones of nearest RHS 186A; center nearest RHS 146B and in high ultraviolet light exposure nearest RHS 138B with spots becoming blushed with a blend nearest RHS N186C and RHS N187C.

*Adaxial* (*young*).—in low ultraviolet light margin between RHS 155C and RHS 155B and in high ultraviolet light developing overtones of nearest RHS 186A; center nearest RHS 138A and in high ultraviolet light exposure nearest RHS 146D with blush of nearest RHS N186C and spots of a blend between RHS N186C and RHS N187A becoming more dense and numerous with greater ultraviolet light exposure.

*Abaxial* (*young*).—In low ultraviolet light exposure margin between RHS 155C and RHS 155B and in high ultraviolet light developing overtones of nearest RHS 186A; center nearest RHS 138B and in high ultraviolet light exposure nearest RHS 138B with spots becoming blushed with a blend nearest RHS N186C and RHS N187C.

Teeth (marginal): Small, about 0.2 mm long, 0.2 mm wide and about 0.5 mm apart; color nearest RHS 155C adaxial and abaxial;

Apical spine: Flexible, frequently drying in older leaves, about 2.5 mm long and 0.7 mm across; some drying in older leaves; color variable, nearest RHS 177B;

Petiole: Sessile;

Veins: Parallel; not distinct abaxial or adaxial;

Flower description: Not yet observed;

Fruit and seed: Not yet observed;

Disease resistance: X *Mangave* 'Wigging Out' has not been observed to be resistant to diseases beyond that which is normal for X *Mangave, Agave* or *Manfreda*. The plant is xeromorphic and survives well with minimal water once established. The new plant is hardy at least from USDA zone 8 to 10. Full extent of winter hardiness has not been tested.

It is claimed:

1. A new and distinct cultivar of ornamental X *Mangave* plant named 'Wigging Out' as herein described and illustrated.

* * * * *